US009353105B2

(12) United States Patent
Chen et al.

(10) Patent No.: US 9,353,105 B2
(45) Date of Patent: May 31, 2016

(54) COMPLEX TARGETING HEPATITIS B VIRUS

(71) Applicant: Shanghai Ai Qi Ecological Technology Co., Ltd., Shanghai (CN)

(72) Inventors: Gong Chen, Shanghai (CN); Kunyuan Song, Shanghai (CN)

(73) Assignee: Shanghai Ai Qi Ecological Technology Co., Ltd., Shanghai (CN)

( * ) Notice: Subject to any disclaimer, the term of this patent is extended or adjusted under 35 U.S.C. 154(b) by 155 days.

(21) Appl. No.: 14/351,575

(22) PCT Filed: Feb. 13, 2014

(86) PCT No.: PCT/CN2014/072012
§ 371 (c)(1),
(2) Date: Apr. 14, 2014

(87) PCT Pub. No.: WO2014/190782
PCT Pub. Date: Dec. 4, 2014

(65) Prior Publication Data

US 2015/0353536 A1 Dec. 10, 2015

(30) Foreign Application Priority Data

May 30, 2013 (CN) .......................... 2013 1 0209943

(51) Int. Cl.

| | |
|---|---|
| ***C07D 421/04*** | (2006.01) |
| ***A61K 31/095*** | (2006.01) |
| ***C07C 391/00*** | (2006.01) |
| ***C07D 311/62*** | (2006.01) |
| ***A61K 31/366*** | (2006.01) |
| ***C01B 19/00*** | (2006.01) |

(52) U.S. Cl.
CPC ............ *C07D 421/04* (2013.01); *A61K 31/095* (2013.01); *A61K 31/366* (2013.01); *C01B 19/008* (2013.01); *C07C 391/00* (2013.01); *C07D 311/62* (2013.01); *C07C 2102/42* (2013.01)

(58) Field of Classification Search
CPC ............................ C07D 421/04; A61K 31/095
See application file for complete search history.

(56) References Cited

U.S. PATENT DOCUMENTS

| | | | | |
|---|---|---|---|---|
| 6,953,786 B2 * | 10/2005 | Pandol | ................ | A61K 31/192 514/183 |
| 8,193,157 B2 * | 6/2012 | Balzarini | ............ | A61K 31/165 514/23 |

* cited by examiner

*Primary Examiner* — Golam M M Shameem

(57) ABSTRACT

A compound medicine for treating acute and chronic hepatitis B, includes a polyphenolic selenium compound having a functional group of alkali metal ion and selenium coordination complex, which has functions of directly killing HBV and destroying replication template of HBV. Auxiliary formulas thereof include high-purity oxymatrine and glycyrrhizin sulfate. The oxymatrine has an effect of anti-HBV, and is capable of treating acute and chronic hepatitis B, regulating immune system and increasing leukocyte. Serving as a main hepatocyte membrane protective agent, the glycyrrhizin sulfate has not only an effect of anti-inflammation, but also it is capable of regulating immune system and protecting hepatocyte. The compound medicine has no toxicity or side effect.

14 Claims, 2 Drawing Sheets

| Number | Retention time | Peak height mAU | Peak area mAU*min | Retention area |
|---|---|---|---|---|
| 1 | 1.28 | 44.314 | 7.860 | 7.440 |
| 2 | 1.65 | 215.357 | 15.577 | 14.743 |
| 3 | 1.97 | 23.812 | 2.343 | 2.217 |
| 4 | 2.23 | 3.650 | 0.381 | 0.361 |
| 5 | 4.27 | 0.616 | 0.084 | 0.080 |
| 6 | 4.97 | 0.298 | 0.032 | 0.031 |
| 7 | 5.22 | 1.047 | 0.168 | 0.159 |
| 8 | 5.70 | 0.239 | 0.032 | 0.030 |
| 9 | 6.00 | 0.260 | 0.044 | 0.041 |
| 10 | 6.60 | 0.626 | 0.094 | 0.089 |
| 11 | 7.03 | 0.649 | 0.116 | 0.110 |
| 12 | 8.45 | 1.355 | 0.481 | 0.455 |
| 13 | 9.20 | 2.926 | 0.626 | 0.593 |
| 14 | 9.62 | 0.392 | 0.050 | 0.047 |
| 15 | 10.03 | 308.179 | 67.898 | 64.264 |
| 16 | 10.70 | 2.267 | 0.407 | 0.385 |
| 17 | 11.03 | 1.159 | 0.346 | 0.327 |
| 18 | 11.62 | 0.329 | 0.048 | 0.045 |
| 19 | 12.77 | 0.667 | 0.086 | 0.081 |
| 20 | 13.18 | 1.257 | 0.203 | 0.192 |
| 21 | 14.08 | 2.112 | 0.516 | 0.488 |
| 22 | 15.05 | 0.168 | 0.044 | 0.041 |
| 23 | 15.37 | 0.291 | 0.035 | 0.033 |
| 24 | 15.53 | 0.237 | 0.031 | 0.029 |
| 25 | 16.03 | 1.981 | 0.297 | 0.281 |
| 26 | 16.28 | 0.100 | 0.014 | 0.013 |
| 29 | 17.68 | 2.266 | 0.433 | 0.410 |
| 30 | 18.12 | 8.509 | 1.251 | 1.184 |
| 31 | 23.07 | 1.581 | 0.216 | 0.205 |
| 32 | 23.47 | 0.514 | 0.063 | 0.060 |
| 33 | 26.57 | 0.706 | 0.153 | 0.145 |
| 34 | 28.67 | 2.931 | 0.472 | 0.447 |
| Total: | | 670.323 | 105.655 | 100.00 |

Fig. 2

COMPLEX TARGETING HEPATITIS B VIRUS

CROSS REFERENCE OF RELATED APPLICATION

This is a Continuation-In-Parts application of an application having an application number PCT/CN2013/078719, filed Jul. 3, 2013, which claims priority under 35 U.S.C. 119(a-d) to CN 201310147738.6, filed Apr. 25, 2013.

BACKGROUND OF THE PRESENT INVENTION

1. Field of Invention

The present invention relates to a medicine for treating hepatitis B, and particularly to a polyphenolic selenium compound having a functional group of alkali metal ion and selenium coordination complex targeting hepatitis B virus.

2. Description of Related Arts

Hepatitis B virus (HBV) is a species of genus *Orthohepadnavirus* causing acute or chronic hepatitis B of human beings. The hepatitis B is a disease caused by HBV. Currently, there is no medicine capable of completely curing hepatitis B. Only a few medicines are capable of assisting patients in fighting against and inhibiting HBV to control their symptoms. Currently, only a small kind of medicine is capable of targeting hepatitis B virus and the treatment effect thereof is far from satisfactory.

SUMMARY OF THE PRESENT INVENTION

An object of the present invention is to provide a complex capable of targeting hepatitis B virus, comprising a principal component of alkali metal ion and selenium coordination complex, and supplementary components of glycyrrhizin sulfate and oxymatrine.

Another object of the present invention is to provide an organic selenium compound with therapeutic effects on hepatitis B.

Accordingly, in order to attain the above objects, the present invention provides a complex targeting hepatitis B virus, comprising a polyphenolic selenium compound having a functional group of alkali metal ion and selenium coordination complex which has a basic structure of an aromatic ring, wherein:

the aromatic ring comprises at least two functional groups, each of which is one member selected from the group consisting of oxygen functional group, sulphur functional group, phosphorus functional group and nitrogen functional group; and a selenium coordination complex functional group is formed by selenium, alkali metal ion and the mentioned functional groups.

Beneficial effects of the present invention are described as follows. The polyphenolic selenium compound having a functional group of alkali metal ion and selenium coordination complex of the present invention has characteristics of over 20% selenium content and no toxicity, and has revolutionary effects in killing virus, enhancing human immunity and etc.

These and other objectives, features, and advantages of the present invention will become apparent from the following detailed description, the attached illustrations, and the appended claims.

BRIEF DESCRIPTION OF THE DRAWINGS

FIG. 2 is illustrations of FIG. 1.

DETAILED DESCRIPTION OF THE PREFERRED EMBODIMENT

Figure 1:
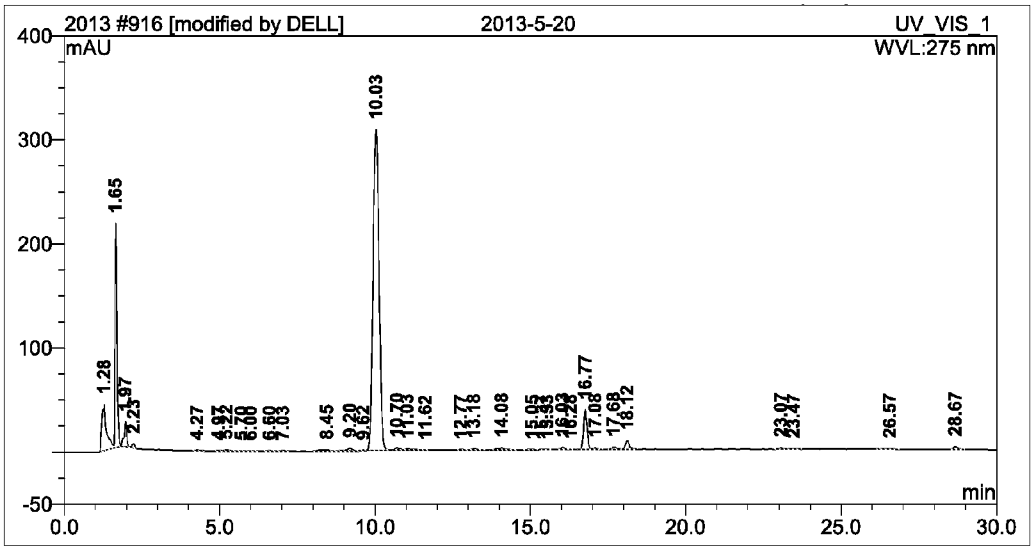
FIG. 1 is a high performance liquid chromatography diagram of a complex targeting hepatitis B virus according to a preferred embodiment of the present invention.

According to a preferred embodiment of the present invention, a complex targeting hepatitis B virus comprising a principal component of a polyphenolic selenium compound having a functional group of alkali metal ion and selenium coordination complex, and supplementary components of glycyrrhizin sulfate and oxymatrine, wherein a basic structure of the polyphenolic selenium compound having a functional group of alkali metal ion and selenium coordination complex has an aromatic ring, wherein the aromatic ring comprises at least two functional groups, each of which is one member selected from the group consisting of oxygen functional group, sulphur functional group, phosphorus functional group and nitrogen functional group; and selenium coordination complex functional group is formed by selenium, alkali metal ion and the mentioned functional groups.

According to a preferred embodiment of the present invention, a preparing method of the polyphenolic selenium compound having a functional group of alkali metal ion and selenium coordination complex comprises following steps of:

a) hydrolyzing lignin to obtain multiple-structural polyphenolic compounds;

b) reacting the multiple-structural polyphenolic compounds with at least one kind of inorganic metal base to obtain multivalent phenolic hydroxyl carboxylate; and c) reacting the multivalent phenolic hydroxyl carboxylate with $SeO_2$ to obtain multivalent phenolic hydroxyl carboxylic acid selenium coordination complex salts, wherein the multivalent phenolic hydroxyl carboxylic acid selenium coordination complex salts are the organic selenium composition.

According to another preferred embodiment of the present invention, the complex targeting hepatitis B virus further comprises oxymatrine and glycyrrhizin sulfate.

Preferably, a purity of the oxymatrine≥95%, a purity of the glycyrrhizin sulfate≥98%, a mass fraction of the oxymatrine has a range of 15~50%, a mass fraction of the glycyrrhizin sulfate has a range of 10~50%, and a mass fraction of the polyphenolic selenium compound having the functional group of alkali metal ion and selenium coordination complex has a range of 5~40%.

1. The oxymatrine has direct function of anti-HBV.
2. The oxymatrine is capable of inhibiting activity of collagen and preventing fibrosis of liver.
3. The oxymatrine is capable of blocking abnormal apoptosis of liver cells.
4. The oxymatrine has a protective effect on liver failure of experimental mice.
5. The oxymatrine is capable of treating chronic hepatitis.
6. The oxymatrine is capable of regulating the function of immunity and increasing the amount of leukocyte in virtue of its anti-inflammatory and antiallergenic properties.
7. The glycyrrhizin sulfate is capable of protecting membrane structure of liver cells.
8. The glycyrrhizin sulfate has effects of anti-HBV and preventing allergic reactions caused by the HBV.
9. The glycyrrhizin sulfate is capable of improving hepatic function.

According to a preferred embodiment of the present invention, the polyphenolic selenium compound having a functional group of alkali metal ion and selenium coordination complex is illustrated, wherein the oxygen functional group comprises: hydroxyl, carboxylic group, phenolic group, quinonyl, quinonyl and hydroxyl, alcoholic hydroxyl, phenolic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group.

According to a preferred embodiment of the present invention, the polyphenolic selenium compound having a functional group of alkali metal ion and selenium coordination complex comprises the following structure of:

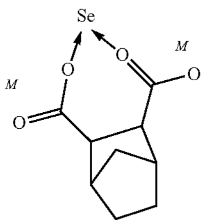

wherein M is alkali metal ion.

According to a preferred embodiment of the present invention, the polyphenolic selenium compound having a functional group of alkali metal ion and selenium coordination complex comprises the following structure of:

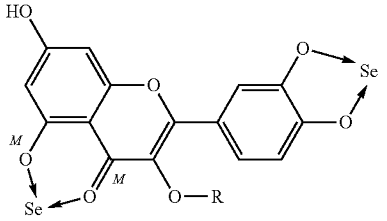

wherein $R{=}CH_3.CH_2CH_2CH_3$.

According to a preferred embodiment of the present invention, the polyphenolic selenium compound having a functional group of alkali metal ion and selenium coordination complex comprises the following structure of:

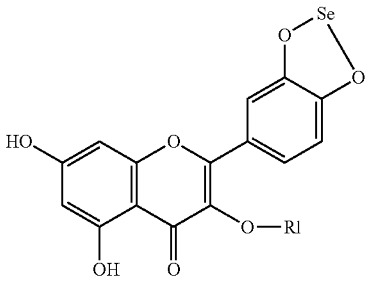

wherein R is a functional segment of alkali metal ion and selenium coordination complex.

According to a preferred embodiment of the present invention, the polyphenolic selenium compound having a functional group of alkali metal ion and selenium coordination complex is illustrated, wherein R has the following structure of:

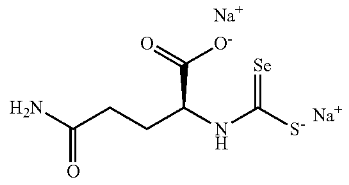 [SMILES: [Na+] ; NC(=O)CC[C@H](NC([S-])=[Se])C(=O)[O-] ; [Na+]]

According to a preferred embodiment of the present invention, the polyphenolic selenium compound having a functional group of alkali metal ion and selenium coordination complex is illustrated, wherein R has the following structure of:

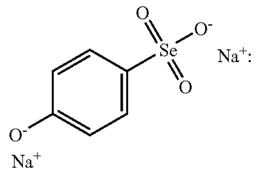

According to a preferred embodiment of the present invention, the polyphenolic selenium compound having a functional group of alkali metal ion and selenium coordination complex is illustrated, wherein R has the following structure of:

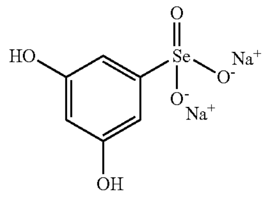

According to a preferred embodiment of the present invention, the polyphenolic selenium compound having a functional group of alkali metal ion and selenium coordination complex is illustrated, wherein R has the following structure of:

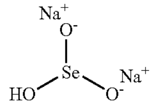

According to a preferred embodiment of the present invention, the polyphenolic selenium compound having a functional group of alkali metal ion and selenium coordination complex is illustrated, wherein R has the following structure of:

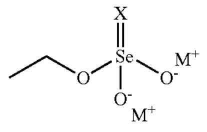

wherein M is alkali metal ion, X is N, S or P.

According to a preferred embodiment of the present invention, the polyphenolic selenium compound having a functional group of alkali metal ion and selenium coordination complex is illustrated, wherein its molecular weight thereof is 100~600.

According to a preferred embodiment of the present invention, aqueous solution of the polyphenolic selenium compound having a functional group of alkali metal ion and selenium coordination complex is weakly alkaline, pH thereof is 7.2~8.5, water-solubility thereof is high, and lipophilicity thereof is good.

According to a preferred embodiment of the present invention, a preparing process of the polyphenolic selenium compound having a functional group of alkali metal ion and selenium coordination complex comprises following steps of:

1. obtaining one kind of multiple-structural polyphenolic compound by means of biotechnological hydrolysis, wherein the multiple-structural polyphenolic compound is weakly acidic (pH: 4.5~6.5), and has good water-solubility, wherein:

molecules of the multiple-structural polyphenolic compound have aromatic rings or other heterocycles such aspyrrole, furan, indole and etc.; the aromatic rings are connected by bridge bond; the aromatic rings may have a variety of active functional groups comprising: hydroxyl, carboxylic group, phenolic group, phenolic hydroxyl, quinonyl, quinonyl and hydroxyl, alcoholic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group;

2. reacting the multiple-structural polyphenolic compound with at least one kind of inorganic alkali metal to obtain low-aromaticity multivalent phenolic hydroxyl carboxylate, which is polymeric, nonhomogeneous, alkaline (pH: 10~12), has high solubility and is capable of dissolving into multiple solvents;

3. reacting the multivalent phenolic hydroxyl carboxylate with $SeO_2$ to obtain low-aromaticity multivalent phenolic hydroxyl carboxylic acid selenium coordination complex salts, wherein a functional group thereof is alkali metal ion and selenium coordination complex, aqueous solution thereof is weakly alkaline (pH: 7.2~8.0), water solubility thereof is high, and lipophilicity thereof is good;

wherein the multivalent phenolic hydroxyl carboxylic acid selenium coordination complex salts consist of a plurality of polyphenolic structures with functional fragments of alkali metal ion and selenium coordination complex.

Fundamental structure of the polyphenolic selenium compound having a functional group of alkali metal ion and selenium coordination complex is bigeminal or poly-phenolic hydroxyl, methoxyl, carboxylic group, quinonyl and hydroxyl and etc.

The polyphenolic selenium compound having the functional group of alkali metal ion and selenium coordination complex is newly produced compound.

Principle of the present invention is as follows. Taking advantage of isosteric principle, N, S or P in functional groups of the multiple-structural polyphenolic compounds is replaced by Se, or N, S or P in the functional groups of the multiple-structural polyphenolic compounds is connected with Se by covalent bond to form the alkali metal ion and selenium coordination complex.

The alkali metal ion forms bidentate or multidentate coordinate bond with O, S, N or P, and O also forms bidentate or multidentate coordinate bond with Se.

Example 1

A polyphenolic selenium compound having a functional group of alkali metal ion and selenium coordination complex has the following structure of:

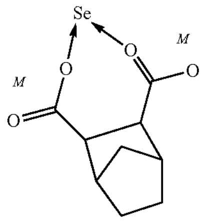

wherein M is alkali metal ion.

In this example, the structure

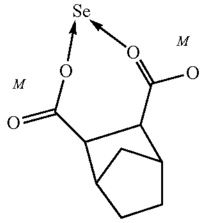

is capable of serving as a functional group R in other structures.

In this example, a preparing process of the polyphenolic selenium compound having the functional group of alkali metal ion and selenium coordination complex comprises following steps of:

a) adding 2.0% urea into lignosulfonate-water solution containing 20% solid formation for serving as growth medium (pH=6.0), wherein the lignosulfonate-water solution is extracted from depickling paper pulp by sulphuric acid; inoculating the growth medium with 2% mixed strains comprising: *candida tropicalis, pseudomonas, candida utilis* and strains of effective microorganisms from Japan, and fermenting for 72 hours under a temperature of 30° C. to obtain the multiple-structural polyphenolic compounds, wherein an inoculation proportion thereof is 1:2:2:2; and b) reacting the multiple-structural polyphenolic compounds with sodium hydroxide to obtain multivalent phenolic hydroxyl sodium carboxylate, wherein multiple-structural polyphenolic compounds:sodium hydroxide=1:1~0.1, wherein a reaction temperature thereof is 120° C., and materials are mechanically stirred to be uniformly mixed while reacting; and c) reacting the multivalent phenolic hydroxyl sodium carboxylate with $SeO_2$ to obtain multivalent phenolic hydroxyl carboxylic acid selenium coordination complex salts, wherein the multivalent phenolic hydroxyl carboxylic acid selenium coordination complex salts are organic selenium composition, multivalent phenolic hydroxyl sodium carboxylate: $SeO_2$=1:1~0.1, a reaction temperature thereof is 150° C., and materials are mechanically stirred to be uniformly mixed while reacting.

Moreover, other various structures of compounds of the present invention are also obtained by means of the above mentioned preparing process of the polyphenolic selenium compound having the functional group of alkali metal ion and selenium coordination complex.

The above produced polyphenolic selenium compound having a functional group of alkali metal ion and selenium coordination complex is mixed with oxymatrine and glycyrrhizin sulfate and then dried, in such a manner that the complex targeting hepatitis B virus of the present invention is obtained.

Example 2

A polyphenolic selenium compound having a functional group of alkali metal ion and selenium coordination complex has the following structure of:

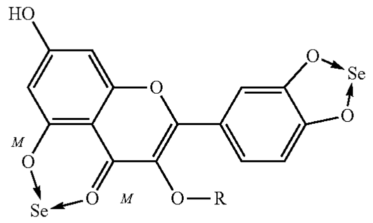

wherein R═$CH_3.CH_2CH_2CH_3$.

In this example, a preparing process of the polyphenolic selenium compound having the functional group of alkali metal ion and selenium coordination complex comprises following steps of:

a) adding 2.0% urea into lignosulfonate-water solution containing 20% solid formation for serving as growth medium (pH=6.0), wherein the lignosulfonate-water solution are extracted from depickling paper pulp by sulphuric acid; inoculating the growth medium with 2% mixed strains comprising: *candida tropicalis, pseudomonas, candida utilis* and strains of effective microorganisms from Japan, and fermenting for 72 hours under a temperature of 30° C. to obtain the multiple-structural polyphenolic compounds, wherein an inoculation proportion thereof is 1:2:2:2; and b) reacting the multiple-structural polyphenolic compounds with potassium hydroxide to obtain multivalent phenolic hydroxyl potassium carboxylate, wherein multiple-structural polyphenolic compounds:potassium hydroxide=1: 1~0.1, wherein a reaction temperature thereof is 120° C., and materials are mechanically stirred to be uniformly mixed while reacting; and c) reacting the multivalent phenolic hydroxyl potassium carboxylate with $SeO_2$ to obtain multivalent phenolic hydroxyl carboxylic acid selenium coordination complex salts, wherein the multivalent phenolic hydroxyl carboxylic acid selenium coordination complex salts are organic selenium composition, multivalent phenolic hydroxyl potassium carboxylate: $SeO_2$=1:1~0.1, a reaction temperature thereof is 140° C., and materials are mechanically stirred to be uniformly mixed while reacting.

Moreover, other various structures of compounds of the present invention are also obtained by means of the above mentioned preparing process of the polyphenolic selenium compound having the functional group of alkali metal ion and selenium coordination complex.

The above produced polyphenolic selenium compound having a functional group of alkali metal ion and selenium coordination complex is mixed with oxymatrine and glycyrrhizin sulfate and then dried, in such a manner that the complex targeting hepatitis B virus of the present invention is obtained.

Example 3

A polyphenolic selenium compound having a functional group of alkali metal ion and selenium coordination complex has the following structure of:

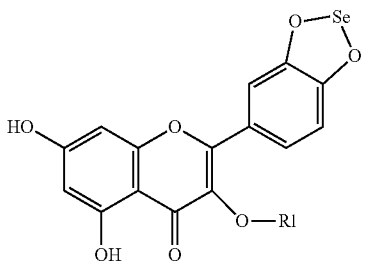

wherein R is a functional fragment of alkali metal ion and selenium coordination complex.

In this example, a preparing process of the polyphenolic selenium compound having the functional group of alkali metal ion and selenium coordination complex comprises following steps of:

a) adding 2.0% urea into lignosulfonate-water solution containing 20% solid formation for serving as growth medium (pH=6.0), wherein the lignosulfonate-water solution are extracted from depickling paper pulp by sulphuric acid; inoculating the growth medium with 2% mixed strains comprising: *candida tropicalis, pseudomonas, candida utilis* and strains of effective microorganisms from Japan, and fermenting for 72 hours under a temperature of 30° C. to obtain the multiple-structural polyphenolic compounds, wherein an inoculation proportion thereof is 1:2:2:2; and b) reacting the multiple-structural polyphenolic compounds with at least one kind of inorganic metal base such as NaOH or KOH to obtain multivalent phenolic hydroxyl sodium carboxylate or multivalent phenolic hydroxyl potassium carboxylate, etc.; and c) reacting the multivalent phenolic hydroxyl sodium/potassium carboxylate and etc. with $SeO_2$ to obtain multivalent phenolic hydroxyl carboxylic acid selenium coordination complex salts comprising Na or K or other alkali metal, wherein the multivalent phenolic hydroxyl carboxylic acid selenium coordination complex salts are organic selenium composition, multivalent phenolic hydroxyl carboxylic acid selenium coordination complex salts comprising alkali metal: $SeO_2$=1:1~0.1, a reaction temperature thereof is 140° C., and materials are mechanically stirred to be uniformly mixed while reacting.

Moreover, other various structures of compounds of the present invention are also obtained by means of the above mentioned preparing process of the polyphenolic selenium compound having the functional group of alkali metal ion and selenium coordination complex.

The above produced polyphenolic selenium compound having a functional group of alkali metal ion and selenium coordination complex is mixed with oxymatrine and glycyrrhizin sulfate and then dried, in such a manner that the complex targeting hepatitis B virus of the present invention is obtained.

After taking the complex targeting hepatitis B virus obtained according to a preferred embodiment of the present invention, following volunteers all achieve effective therapeutic results.

Therapeutic Effects of the Medicine on Volunteers

| Volunteer 1 | Sex: male | Age: 62 |
|---|---|---|

The volunteer takes 0.4 g solid capsule of the complex targeting hepatitis B virus twice daily, morning and evening, wherein the polyphenolic selenium compound having the functional group of alkali metal ion and selenium coordination complex is prepared according to the preferred embodiment 1 of the present invention, a purity of the oxymatrine is 95%, a mass fraction of the oxymatrine is 40%, a purity of the glycyrrhizin sulfate is 98%, a mass fraction of the glycyrrhizin sulfate is 40%, and a mass fraction of the polyphenolic selenium compound having the functional group of alkali metal ion and selenium coordination complex is 20%.

Medical Examination Result Prior to the Medicine Administration
May 11, 2012

| Code of item | Name of item | Result | Reference value | Unit |
|---|---|---|---|---|
| HBV-DNA | DNA of HBV | 4.48E+06 | <1.0*10^3 | copies/ml |

Medical Examination Result Posterior to the Medicine Administration
Sep. 10, 2012

| Code of item | Name of item | Result | Unit | Minimum detection limit |
|---|---|---|---|---|
| HBV-DNA | DNA of HBV | Less than minimum detection limit | IU/ml | 5.00E^2 |

Medical Diagnostics Prior to the Medicine Administration

The maximum value of fasting blood glucose is 19.3, and the value of 2-hour postprandial blood glucose reaches 35.4. The volunteer carries hepatitis B virus.

Symptoms prior to the medicine administration: myasthenia of limbs, dry mouth, thirsty, frequent micturition, hunger, sweating due to debility, marasmus and insomnia. After therapy with insulin at hospital, the blood glucose has become normal. The volunteer takes entecavir for treating hepatitis.

Self-description by the volunteer is as follows. Appetite, defecation, sleep, stamina and emotion are all in normal condition. The volunteer 1 feels good, his limbs are powerful, his motion is normal. The volunteer 1 plays ping-pong every day. The past abnormal symptoms disappear, no abnormal feelings now.

Onset time of curative effect: 20 days posterior to the medicine administration, it took effect. After continuous administration of the medicine for 50 days, the patient is cured.

Medical Examination Result Posterior to Drug Withdrawal for 3 Months
Dec. 24, 2012

| Code of item | Name of item | Result | Unit | Minimum detection limit |
|---|---|---|---|---|
| HBV-DNA | DNA of HBV | Less than minimum detection limit | IU/ml | 5.00E^2 |

Volunteer 2 Sex: male Age: 41 Medical record: hepatitis B cirrhosis

The volunteer takes 0.4 g solid capsule of the complex targeting hepatitis B virus twice daily, morning and evening, wherein the polyphenolic selenium compound having the functional group of alkali metal ion and selenium coordination complex is prepared according to the preferred embodiment 1 of the present invention, a purity of the oxymatrine is 95%, a mass fraction of the oxymatrine is 40%, a purity of the glycyrrhizin sulfate is 98%, a mass fraction of the glycyrrhizin sulfate is 40%, and a mass fraction of the polyphenolic selenium compound having the functional group of alkali metal ion and selenium coordination complex is 20%.

Medical Examination Result Prior to the Medicine Administration
Jan. 11, 2013

| Item name | Item for short | Result | Unit | Reference value |
|---|---|---|---|---|
| Hepatitis B virus DNA quantity | HBV-DNA | $9.36 \times 10^2$ | IU/ml | <40 |
| Total protein | TP | 83 | g/L | 60~83 |
| Albumin | ALB | 46 | g/L | 35~55 |
| Globulin | GLO | 36 | g/L | |
| Ratio of albumin to globulin | A/G | 1.28 | | |
| Prealbumin | PAL | 142↓ | mg/L | 160~400 |
| Direct bilirubin | DBIL | 19.2↑ | umol/L | 0~6.8 |
| Total bilirubin | TBIL | 41.7↑ | umol/L | 3.4~20.5 |
| Ratio of direct to total bilirubin | D/T | 0.46 | | |
| Alanine aminotransferase | ALT | 404↑ | U/L | 5~40 |
| Aspartate aminotransferase | AST | 270↑ | U/L | 8~40 |
| Ratio of AST/ALT | S/T | 0.67 | | |
| Alkaline phosphatase | ALP | 138 | U/L | 40~150 |
| R-glutamyl transpeptidase | GGT | 88↑ | U/L | 11~50 |
| Total bile acid | TBA | 26↑ | umol/L | 0~10 |
| Cholinesterase | CHE | 5998 | U/L | 5400~13200 |
| Lactate dehydrogenase | LDH | 221 | U/L | 109~245 |
| 5'-ribonuclease | 5NT | 6 | U/L | 0~10 |
| Adenosine deaminase | ADA | 51↑ | U/L | 0~20 |
| Urea | UREA | 4.6 | mmol/L | 2.9~8.2 |
| Creatinine | CRE | 87 | umol/L | 62~115 |
| Uric acid | UA | 317 | umol/L | 208~428 |
| Alpha-fetoprotein | AFP | 14 | ng/ml | 0~20 |
| Leukocyte | WBC | 5.01 | $10^9$/L | 4~10 |
| Leutrophils percentage | NE % | 0.637 | | 0.5~0.7 |
| Absolute neutrophil count | NE# | 3.2 | $10^9$/L | 2~7 |
| Lymphocyte percentage | LY % | 0.201 | | 0.2~0.4 |
| Absolute lymphocyte count | LY# | 1.01 | $10^9$/L | 0.8~4.0 |
| Monocytes percentage | M0 % | 0.087 | | 0.03~0.1 |
| Absolute monocytes count | M0# | 0.43 | $10^9$/L | 0.12~1.0 |
| Eosinophils percentage | E0 % | 0.069↑ | | 0.005~0.05 |
| Absolute eosinophils count | E0 | 0.35 | $10^9$/L | 0.02~0.5 |
| Basophil percentage | BA % | 0.006 | | 0~0.01 |
| Absolute basophil count | BA# | 0.03 | $10^9$/L | 0~0.1 |
| Erythrocyte | RBC | 4.95 | $10^{12}$/L | 4~5.5 |
| Hemoglobin | HGB | 161.00 | g/L | 131~172 |
| Hematocrit | HCT | 48.10 | % | 38~50.8 |
| Mean corpuscular volume | | 97.2 | fL | 82.6~99.1 |
| Corpuscular hemoglobin concentration | | 336 | g/L | 320~362 |
| Mean corpuscular hemoglobin | | 32.6 | pg | 26.9~33.8 |
| Erythrocyte hemoglobin distribution width | | 14.6 | % | 0~15 |

-continued

| Medical Examination Result Prior to the Medicine Administration Jan. 11, 2013 | | | | |
|---|---|---|---|---|
| Item name | Item for short | Result | Unit | Reference value |
| Platelet | PLT | 102.00 | 10^9/L | 100~300 |
| Thrombocytocrit | | 0.099 | | 0.06~0.40 |
| Mean platelet volume | | 9.7 | fL | 7.54~11.2 |
| Platelet distribution width | PDW | 11.2 | % | 9.0~18.0 |
| Platelet large cell ratio | P-LCR | 24.5 | % | 13~43 |

| Medical Examination Result Posterior to the Medicine Administration for One Month Testing method: fluorescent quantitative nucleic acid testing Testing time: Feb. 8, 2013 | | | | |
|---|---|---|---|---|
| Name of item | Item | Result | Unit | Reference value |
| Fluorescent quantitative nucleic acid testing HBV | HBV-DNA | 1.14 × 10^2 | IU/ml | <40 |
| Item name | Item for short | Result | Unit | Reference value |
| Total protein | TP | 76 | g/L | 60~83 |
| Albumin | ALB | 45 | g/L | 35~55 |
| Globulin | GLO | 32 | g/L | |
| Ratio of albumin to globulin | A/G | 1.42 | | |
| prealbumin | PAL | 159↓ | mg/L | 160~400 |
| Direct bilirubin | DBIL | 9.6↑ | umol/L | 0~6.8 |
| Total bilirubin | TBIL | 20.1↑ | umol/L | 3.4~20.5 |
| Ratio of direct to total bilirubin | D/T | 0.48 | | |
| Alanine aminotransferase | ALT | 58↑ | U/L | 5~40 |
| Aspartate aminotransferase | AST | 44↑ | U/L | 8~40 |
| Ratio of AST/ALT | S/T | 0.80 | | |
| Alkaline phosphatase | ALP | 114 | U/L | 40~150 |
| r-glutamyl transpeptidase | GGT | 44↑ | U/L | 11~50 |
| Total bile acid | TBA | 30↑ | umol/L | 0~10 |
| Cholinesterase | CHE | 6752 | U/L | 5400~13200 |
| Lactate dehydrogenase | LDH | 157 | U/L | 109~245 |
| 5'-ribonuclease | 5NT | 3 | U/L | 0~10 |
| Adenosine deaminase | ADA | 37↑ | U/L | 0~20 |
| Urea | UREA | 3.6 | mmol/L | 2.9~8.2 |
| Creatinine | CRE | 91 | umol/L | 62~115 |
| Uric acid | UA | 360 | umol/L | 208~428 |
| Leukocyte | WBC | 4.85 | 10^9/L | 4~10 |
| Leutrophils percentage | NE % | 0.611 | | 0.5~0.7 |
| Absolute neutrophil count | NE# | 3.0 | 10^9/L | 2~7 |
| Lymphocyte percentage | LY % | 0.244 | | 0.2~0.4 |
| Absolute Lymphocyte count | LY# | 1.18 | 10^9/L | 0.8~4.0 |
| Monocytes percentage | M0 % | 0.091 | | 0.03~0.1 |
| Absolute monocytes count | M0# | 0.45 | 10^9/L | 0.12~1.0 |
| Eosinophils percentage | E0 % | 0.050 | | 0.005~0.05 |
| Absolute eosinophils count | E0 | 0.24 | 10^9/L | 0.02~0.5 |
| Basophil percentage | BA % | 0.004 | | 0~0.01 |
| Absolute basophil count | BA# | 0.02 | 10^9/L | 0~0.1 |
| Erythrocyte | RBC | 4.89 | 10^12/L | 4~5.5 |
| Hemoglobin | HGB | 160.00 | g/L | 131~172 |
| Hematocrit | HCT | 47.20 | % | 38~50.8 |
| Mean corpuscular volume | | 96.6 | fL | 82.6~99.1 |
| Corpuscular hemoglobin concentration | | 339 | g/L | 320~362 |
| Mean corpuscular hemoglobin | | 32.8 | pg | 26.9~33.8 |
| Erythrocyte hemoglobin distribution width | | 14.3 | % | 0~15 |
| Platelet | PLT | 94.00↓ | 10^9/L | 100~300 |
| Thrombocytocrit | | 0.088 | | 0.06~0.40 |
| Mean platelet volume | | 9.3 | fL | 7.54~11.2 |
| Platelet distribution width | PDW | 11.0 | % | 9.0~18.0 |
| Platelet large cell ratio | P-LCR | 21.5 | % | 13~43 |

Onset time of curative effect: after a continuous medicine administration for one month, copies of HBV decreased by nearly 90%.

One skilled in the art will understand that the embodiment of the present invention as shown in the illustrations and described above is exemplary only and not intended to be limited.

It will thus be seen that the objects of the present invention have been fully and effectively accomplished. Its embodiments have been shown and described for the purposes of illustrating the functional and structural principles of the present invention and are subject to change without departure from such principles. Therefore, this invention includes all modifications encompassed within the spirit and scope of the following claims.

What is claimed is:

1. A complex targeting hepatitis B virus, comprising a polyphenolic selenium compound having a functional group of alkali metal ion and selenium coordination complex which has an aromatic ring, wherein:

the aromatic ring comprises at least two functional groups, each functional group is one member selected from the group consisting of oxygen functional group, sulphur functional group, phosphorus functional group and nitrogen functional group, and selenium coordination complex functional group formed by selenium, alkali metal ion and the oxygen functional group, the sulphur functional group, the phosphorus functional group or the nitrogen functional group.

2. The complex targeting hepatitis B virus, as recited in claim 1, further comprising oxymatrine and glycyrrhizin sulfate.

3. The complex targeting hepatitis B virus, as recited in claim 2, wherein a purity of the oxymatrine≥95%, a purity of the glycyrrhizin sulfate≥98%, a mass fraction of the oxymatrine has a range of 15~50%, a mass fraction of the glycyrrhizin sulfate has a range of 10~50%, and a mass fraction of the polyphenolic selenium compound having the functional group of alkali metal ion and selenium coordination complex has a range of 5~40%.

4. The polyphenolic selenium compound having a functional group of alkali metal ion and selenium coordination complex, as recited in claim 1, wherein the oxygen functional group comprises: hydroxyl, carboxylic group, phenolic group, quinonyl, quinonyl and hydroxyl, alcoholic hydroxyl, phenolic hydroxyl, sulfonic group, amino group, free quinonyl, semiquinone, quinonic oxygen group, monomethyl, and at least one kind monomethyl-active functional group which comprises methoxyl, carboxymethyl, hydroxymethyl, phenolic methyl and methylamino group.

5. The polyphenolic selenium compound having a functional group of alkali metal ion and selenium coordination complex, as recited in claim 1, wherein a structure thereof comprises

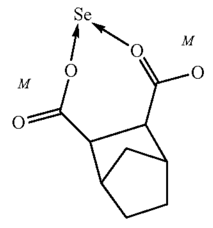

wherein M is alkali metal ion.

6. The polyphenolic selenium compound having a functional group of alkali metal ion and selenium coordination complex, as recited in claim 1, wherein a structure thereof comprises:

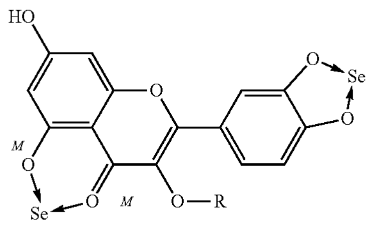

wherein R=$CH_3.CH_2CH_2CH_3$.

7. The polyphenolic selenium compound having a functional group of alkali metal ion and selenium coordination complex, as recited in claim 1, wherein a structure thereof comprises:

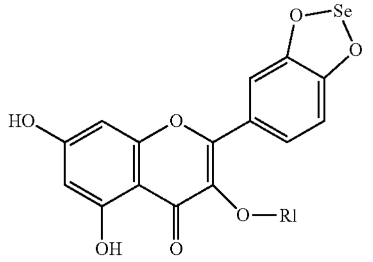

wherein R is alkali metal ion and selenium coordination complex.

8. The polyphenolic selenium compound having a functional group of alkali metal ion and selenium coordination complex, as recited in claim 7, wherein R has following structure of

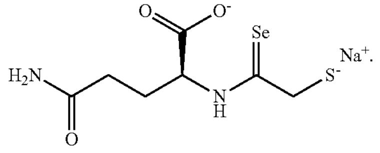

9. The polyphenolic selenium compound having a functional group of alkali metal ion and selenium coordination complex, as recited in claim 7, wherein R has following structure of

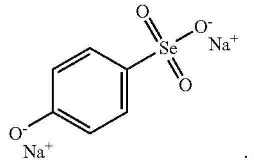 [SMILES: O=[Se](=O)([O-])c1ccc([O-])cc1 ; [Na+] ; [Na+]]

10. The polyphenolic selenium compound having a functional group of alkali metal ion and selenium coordination complex, as recited in claim 7, wherein R has following structure of

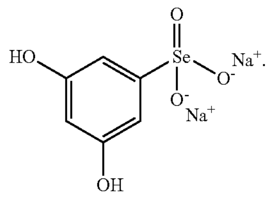

11. The polyphenolic selenium compound having a functional group of alkali metal ion and selenium coordination complex, as recited in claim 7, wherein R has following structure of

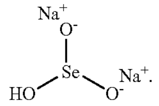

12. The polyphenolic selenium compound having a functional group of alkali metal ion and selenium coordination complex, as recited in claim 7, wherein R has following structure of

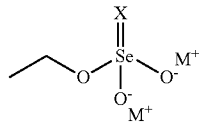

wherein M is alkali metal ion, X is N, S or P.

13. The polyphenolic selenium compound having a functional group of alkali metal ion and selenium coordination complex, as recited in claim 1, wherein a molecular weight thereof is 100~600.

14. A method for treating hepatitis B in a mammal comprising applying a therapeutically effective amount of the polyphenolic selenium compound having a functional group of alkali metal ion and selenium coordination complex as recited in claim 1, or a medicinally acceptable salt thereof to the mammal.

* * * * *